US00PP26806P3

(12) United States Plant Patent

Sato et al.

(10) Patent No.: US PP26,806 P3

(45) Date of Patent: Jun. 7, 2016

(54) **NEW GUINEA *IMPATIENS* PLANT NAMED 'SAKIMP031'**

(50) Latin Name: ***Impatiens hybrida* hort**
Varietal Denomination: SAKIMP031

(71) Applicant: Sakata Seed Corporation, Yokohama (JP)

(72) Inventors: Chihiro Sato, Nagano (JP); Shinji Minemura, Nagano (JP)

(73) Assignee: Sakata Seed Corporation, Yokohama (JP)

( * ) Notice: Subject to any disclaimer, the term of this patent is extended or adjusted under 35 U.S.C. 154(b) by 176 days.

(21) Appl. No.: 13/998,937

(22) Filed: Dec. 23, 2013

(65) Prior Publication Data

US 2015/0181793 P1 Jun. 25, 2015

(51) Int. Cl.
*A01H 5/02* (2006.01)

(52) U.S. Cl.
USPC ..... Plt./318.4

(58) Field of Classification Search
USPC ..... Plt./318.4
See application file for complete search history.

*Primary Examiner* — Keith Robinson
(74) *Attorney, Agent, or Firm* — Barbara Campbell; Bethany R. Roahrig; Cochran Freund & Young, LLC

(57) ABSTRACT

A New Guinea *Impatiens* plant particularly distinguished by having a pink flower color, strong root system and a spreading plant growth habit, is disclosed.

1 Drawing Sheet

Genus and species: *Impatiens hybrida* hort.
Variety denomination: 'SAKIMP031'.

BACKGROUND OF THE NEW PLANT

The present invention comprises of a new and distinct variety of New Guinea *Impatiens*, botanically known as *Impatiens hybrida* hort, and referred to by the variety name 'SAKIMP031'. 'SAKIMP031' originated from a hybridization in September 2009 in Misato, Japan between the proprietary female *Impatiens* breeding line 'NE-4391' (unpatented) having a blush flower color and the proprietary male *Impatiens* breeding line 'NF-4858' (unpatented) having a red flower color.

In September 2009, the female parent line 'NE-4391' and male parent line 'NF-4858' were crossed and a population of $F_1$ plants was created. The $F_1$ plants were evaluated in Misato, Japan in an open field trial. The criteria for plant selection included flower color, a strong root system and a spreading plant growth habit. At the completion of the trial, one single-plant selection was made based on the above criteria and vegetatively propagated. From May to August 2011, the selection was evaluated in an open field in Misato, Japan. Terminal tip vegetative cuttings of the variety were then shipped to Salinas, Calif., where the plants were regenerated and reevaluated for stability of traits. The selection subsequently was named 'SAKIMP031' and was found to have its unique characteristics reproduce true to type in successive generations of asexual propagation via terminal tip vegetative cuttings in Salinas, Calif.

SUMMARY

The following are the most outstanding and distinguishing characteristics of this new variety when grown under normal horticultural practices in Salinas, Calif.

1. Pink flowers;
2. Strong root system; and
3. A spreading plant growth habit.

DESCRIPTION OF THE PHOTOGRAPHS

This *Impatiens* plant is illustrated by the accompanying photographs which show the plant's overall plant habit including form, foliage, and flowers. The photographs are of plants grown about 4-months-old in Salinas, Calif. under greenhouse conditions in the spring of 2013. The colors shown are as true as can be reasonably obtained by conventional photographic procedures.

DESCRIPTION OF THE NEW VARIETY

Figure 1:
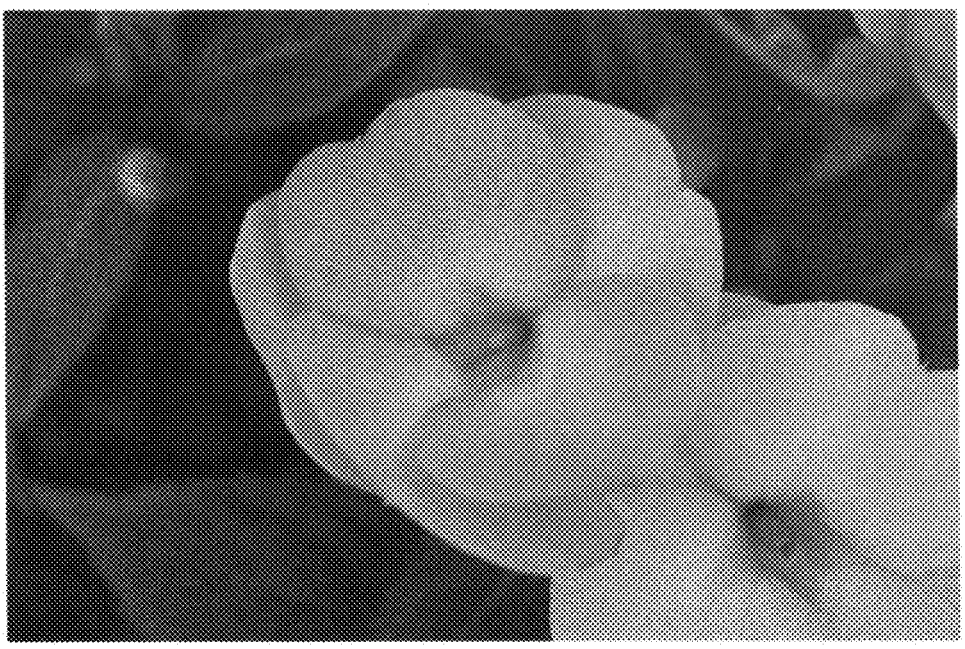
FIG. 1 shows a close-up of the mature inflorescence of the plant.
Figure 2:
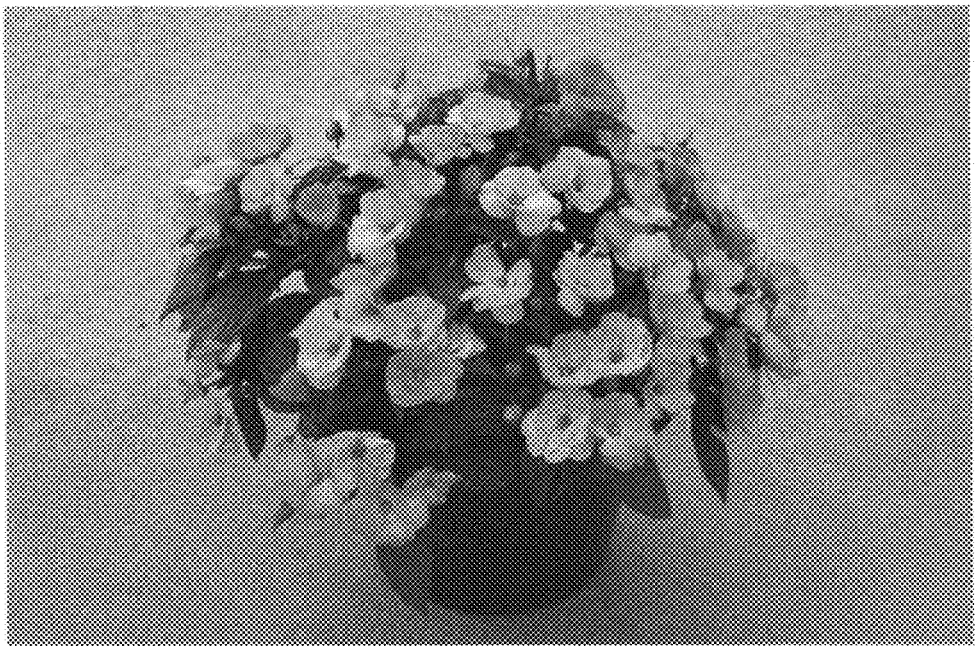
FIG. 2 shows the overall plant habit of the plant grown in a pot.

The following detailed descriptions set forth the distinctive characteristics of 'SAKIMP031'. The data which define these characteristics were collected from asexual reproductions carried out in Salinas, Calif. Data was collected on plants grown about 1 month from transplant date (about 4-months-old) and propagated by terminal tip vegetative cuttings under greenhouse conditions in Salinas, Calif. in the summer of 2013. Color references are to The R.H.S. Colour Chart of The Royal Horticultural Society of London (R.H.S.), $4^{th}$ edition (2001).

Classification:

*Family*.—Balsaminaceae.

*Botanical*.—*Impatiens* interspecific cross (*Impatiens hybrida* hort).

*Common*.—*Impatiens*.

*Designation*.—'SAKIMP031'.

Parentage:

*Female parent*.—Proprietary *Impatiens* line 'NE-4391' (unpatented).

*Male parent*.—Proprietary *Impatiens* line 'NF-4858' (unpatented).

Growth:

*Time to produce a rooted cutting.*—About 4 weeks.

*Time to initiate roots.*—2 weeks.

*Rooting habit.*—Vigorous.

*Root type.*—Fibrous.

*Root color.*—RHS 155A (White).

*Environmental conditions for plant growth.*—The terminal 1.0 to 1.5 inches of an actively growing stem was excised. The vegetative cuttings were propagated in five to six weeks. The base of the cuttings were dipped for 1 to 2 seconds in a 1:9 solution of DIP 'N GROW (1 solution: 9 water) a root inducing solution, immediately prior to sticking into the cell trays. Cuttings were stuck into plastic cell trays having 98 cells, and containing a moistened peat moss-based growing medium. The cuttings were misted with water from overhead for 10 seconds every 30 minutes until sufficient roots were formed. Rooted cuttings were transplanted and grown in 20-cm-diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 20% nitrogen, 10% phosphorus and 18% potassium. The typical average air temperature was 24° C.

*Time to bloom from propagation.*—6 to 8 weeks.

Plant description:

*Habit.*—Spreading.

*Life cycle.*—Annual.

*Height (from soil line to top of foliage).*—24.0 cm.

*Height (from soil line to first node).*—1.0 cm.

*Spread.*—45.0 cm.

*Flowering requirements.*—Will flower so long as temperature is above 5° C.

*Temperature tolerances.*—Plants observed to continue flowering in a temperature range of 5° C. to 36° C. Plants can withstand high heat and humidity.

Branches:

*Number of branches.*—6 main branches.

*General description.*—Smooth, circular cross-section.

*Length of branches.*—9.0 cm.

*Diameter of branches.*—1.0 cm.

*Internodes.*—4.0 cm.

*Color of branches.*—RHS 59A (Red-Purple) with RHS 144B (Yellow-Green).

*Anthocyanin color.*—RHS 59A.

*Pubescence.*—Absent.

*Texture.*—Smooth.

Stems:

*General description.*—Strong; circular cross-section, smooth.

*Stem length.*—11.0 cm.

*Diameter.*—0.5 cm.

*Internode length.*—7.0 cm.

*Color.*—RHS 59B (Red-Purple) with slight RHS 144B (Yellow-Green).

*Pubescence.*—Absent.

*Anthocyanin color.*—RHS 59B (Red-Purple).

Leaves:

*Arrangement.*—Opposite.

*Shape.*—Lanceolate.

*Apex.*—Acute.

*Base.*—Attenuate.

*Margin.*—Entire.

*Surface appearance (both surfaces).*—Dull.

*Surface pubescence (both surfaces).*—Absent; surface is glabrous.

*Length.*—9.0 cm.

*Width.*—3.0 cm.

*Color.*—Upper surface: RHS 147A (Yellow-Green). Lower surface: RHS 147B (Yellow-Green).

*Venation.*—Pinnate.

*Venation color (both surfaces).*—RHS 59D (Red-Purple).

*Variegation.*—Absent.

*Fragrance.*—Absent.

*Petiole.*—Length: 1.0 cm. Diameter: 0.3 cm. Strength: Medium.

Flowers:

*Total number of flowers per node.*—2 to 3 in bloom.

*Inflorescence type.*—Single flower with spur and 5 petals, floriferous.

*Fragrance.*—Absent.

*Pedicel.*—Absent.

Flower bud:

*Surface texture.*—Smooth, glabrous.

*Length.*—1.5 cm.

*Diameter.*—1.3 cm.

*Shape.*—Deltoid.

*Color.*—RHS 59B (Red-Purple) with RHS 58B (Red-Purple) and slight RHS 144A (Yellow-Green) at the edge.

Peduncle:

*Length.*—4.0 cm.

*Width.*—0.2 cm.

*Color.*—RHS 59C (Red-Purple).

*Surface texture.*—Glabrous, smooth.

*Strength.*—Medium.

Corolla:

*Shape.*—Rotate, stellate.

*Diameter.*—5.0 cm.

*Depth.*—2.0 cm.

*Petals.*—Shape: Bi-lobed, curved, recessed at mid-vein. Apex: Obcordate. Margin: Entire. Pubescence (both surfaces): Glabrous. Length: 2.0 cm. Width: 3.0 cm. Color: Upper: RHS 58C (Red-Purple) with some RHS 58D (Red-Purple). Lower: RHS 58C (Red-Purple) with some RHS 58C (Red-Purple). and RHS 59C (Red-Purple) at the mid-veins. Eye zone: RHS 64C (Red-Purple).

Spur:

*Shape.*—Horn-shaped.

*Length.*—4.0 cm.

*Diameter.*—0.2 cm.

*Color.*—RHS 59C (Red-Purple).

*Texture.*—Smooth, glabrous.

*Degree of curvature.*—Medium.

Calyx:

*Arrangement.*—Composed of 2 sepals.

*Sepals.*—Shape: Lanceolate, curled. Apex: Acute. Base: Obtuse. Margin: Entire. Surface texture (both surfaces): Smooth, glabrous. Color: RHS 62B (Red-Purple). Length: 2.0 cm. Diameter: 1.0 cm.

Reproductive organs:

*Stamen number.*—5.

*Stamen form.*—Fused on top of ovary.

*Filament color.*—RHS 58C (Red-Purple).

*Anther color.*—RHS 155A (White).

*Pollen color.*—RHS 155D (White).

*Pollen amount.*—Abundant.

*Ovary arrangement.*—Fused in capsule.

*Ovary surface color.*—RHS 144A (Yellow-Green).

*Ovary shape.*—Ovate.

*Pistil number.*—1.

*Stigma color and shape.*—RHS 155A (White) and hair-like.

*Style color.*—RHS 155A (White).

*Seed production.*—Absent.

Disease and insect resistance: Tolerant to downy mildew (*Plasmopara obducens*).

COMPARISON WITH PARENTAL LINES AND KNOWN VARIETY

'SAKIMP031' is a new and unique variety of *Impatiens* owing to its pink flower color, strong root system and a compact plant growth habit. 'SAKIMP031' is distinguished from its parents mainly by flower color as shown in Table 1 below:

TABLE 1

Comparison with Parental Lines

| Characteristic | 'SAKIMP031' | Female Parent 'NE-4391' | Male Parent 'NF-4858' |
|---|---|---|---|
| Flower color | Pink | Blush | Red |

'SAKIMP031' is a new and unique variety of *Impatiens* owing to its pink flower color, strong root system and a compact plant growth habit. When 'SAKIMP031' compared to the commercial *Impatiens* variety 'SAKIMP022' (U.S. Plant Pat. No. 23,500), the following differences as described in Table 2 below.

TABLE 2

Comparison with Similar Variety

| Characteristic | 'SAKIMP031' | 'SAKIMP022' |
|---|---|---|
| Petal color, upper surface | RHS 58C with some RHS 58D | RHS N57A |
| Petal color, lower surface | RHS 58C with some RHS 58C and RHS 59C at the mid-vein | RHS 58B |
| Petal color, eye zone | RHS 64C | RHS 60A |
| Stem color | RHS 59B with RHS 144B | RHS 187B |

We claim:

1. A new and distinct variety of New Guinea *Impatiens* plant as shown and described herein.

* * * * *